(12) United States Patent
Bouliniere (10) Patent No.: US 8,873,597 B2
(45) Date of Patent: Oct. 28, 2014

(54) METHOD OF CONTROL AND OF POSITIONING WITH THE AID OF LASER SYSTEMS, AND DEVICE FOR IMPLEMENTING SAID METHOD

(75) Inventor: Pascal Bouliniere, Villeroy (FR)

(73) Assignee: Cyrpa International, Bruxelles (BE)

( * ) Notice: Subject to any disclaimer, the term of this patent is extended or adjusted under 35 U.S.C. 154(b) by 0 days.

(21) Appl. No.: 13/984,419

(22) PCT Filed: Feb. 9, 2012

(86) PCT No.: PCT/BE2012/000007
§ 371 (c)(1),
(2), (4) Date: Oct. 21, 2013

(87) PCT Pub. No.: WO2012/106782
PCT Pub. Date: Aug. 16, 2012

(65) Prior Publication Data
US 2014/0044141 A1 Feb. 13, 2014

(30) Foreign Application Priority Data

Feb. 9, 2011 (BE) .................................. 2011/0082

(51) Int. Cl.
*H01S 3/10* (2006.01)
*A61B 6/08* (2006.01)
*A61N 5/10* (2006.01)
*A61B 6/04* (2006.01)
*A61B 6/00* (2006.01)

(52) U.S. Cl.
CPC ................ *A61B 6/08* (2013.01); *A61N 5/1049* (2013.01); *A61B 6/0492* (2013.01); *A61B 6/4405* (2013.01); *A61N 2005/105* (2013.01)

USPC ...................... 372/24; 372/29.01; 372/29.011

(58) Field of Classification Search
USPC .................................... 372/24, 29.01, 29.011
See application file for complete search history.

(56) References Cited

U.S. PATENT DOCUMENTS 5,690,107 A * 11/1997 Hofmann ...................... 600/407
2007/0284543 A1 * 12/2007 Rockseisen ................ 250/491.1

* cited by examiner

*Primary Examiner* — Kinam Park
(74) *Attorney, Agent, or Firm* — Birch, Stewart, Kolasch & Birch, LLP (57) ABSTRACT

A method for adjusting laser beams (4) for scanners arranged on a support for radiotherapy, by a device consisting of a one-piece assembly (1) comprising (3) a suitable electronic control board (8), and position sensors (3) for visualizing the position of the beams (4), and adjusting them automatically by motor-driven systems, which is remarkable in that it comprises the steps of installing the apparatus (1); presetting of the position via 3 support feet (6) and embedded spirit levels (7); movement of the table of the scanner to position the front face (11) of the apparatus in the plane of the isocenter of the scanner and positioning via internal lasers of the scanner; acquisition of position control images of the apparatus (1) and finalization and validation thereof, movement of the table of the scanner by the nominal distance between the machine isocenter and the laser isocenter, which is determined and validated at the time of installation of the lasers; connection of the apparatus (1) and powering up thereof and of the laser beams (4) with 0 resetting of the positions; startup of the multiplexing-based laser beam (4) search sequence, the position of each laser beam (4) then being determined by virtue of the embedded cells (3) in the apparatus (1); acquisition of the values and transfer to the tablet PC of the adjustment phase of each laser beam (4). Device for implementing same.

19 Claims, 7 Drawing Sheets

METHOD OF CONTROL AND OF POSITIONING WITH THE AID OF LASER SYSTEMS, AND DEVICE FOR IMPLEMENTING SAID METHOD

FIELD OF THE INVENTION

The invention relates to an adjustment and positioning method using laser systems, primarily in the radiotherapy sector.

TECHNOLOGICAL BACKGROUND

These days, more than 50% of patients suffering from cancer receive radiotherapy treatment. This treatment may be sufficient in some cases. It may be, however, that the medical team responsible for tracking the patient feels that a surgical ablation of the tumor must follow the radiotherapy treatment.

For nearly a century, radiotherapy has formed a part of the therapeutic arsenal for cancer illnesses. After a few early stutters, this technique is now well controlled and forms, with chemotherapy and surgery, the most widespread cancer treatment, culminating in a large number of recoveries.

The principle of radiotherapy is simple: it entails exposing the cancerous cells to an ionization, that is to say an emission of radiation, which will alter the composition of the genetic information of the cancerous cells. These days, the specialists have at their disposal a very wide range, in terms of quality and quantity, of ionizing radiations.

This genetic material contained in DNA form undergoes transformations which render the irradiated cell incapable of reproducing. This kind of sterilization thus reduces the anarchic reproduction of these malignant cells which are responsible for the cancer. Of course, the normal cells can also be affected by these radiations, but their rates of repair are greater than those of the cancerous cells, which thus produces a so-called differential effect. This differential effect explains the benefit of radiotherapy for the sick. Thus, the mission of the radiotherapist is to succeed in killing the cancerous cells and preserve the healthy cells of the patient.

Radiotherapy can thus be prescribed as a curative treatment, namely to destroy the tumor, as palliative treatment to mitigate the pain, or even as auxiliary treatment to prepare or complement a surgical intervention or chemotherapy.

Before the treatment proper can be followed, the radiotherapy has to be prepared. For this, the location and the dose of radiation which will be administered to the patient have to be determined. In a first step, the treatments are prepared using a scanner, which makes it possible to set the limits of the area that has to be irradiated. A three-dimensional reconstruction of software images will make it possible to locate the tumor very precisely. The patient will have to remain immobile, in order for the locating of the area to be as accurate as possible.

Once the area to be treated is determined, the practician applies to the patient small dots, tattooed or painted, notably using "fuchsine", to identify the area to be treated. This first step takes 30 minutes to an hour. It is at this stage that the positioning lasers are used.

The second step consists in analyzing all the data acquired by the machine for the radiotherapist and the radiophysician to determine the treatment apparatus to be used, the distribution of the dose, the size, the number and orientation of the irradiation fields, which are most appropriate. The quantity of radiation prescribed depends on the age and the state of health of the patient, as well as the location and the type of cancer.

The total dose is then divided up into smaller doses, because the effect is cumulative. The divided-up doses will then be administered in various sessions, to each of them. These sessions will be spread on average over two to seven weeks.

The positioning lasers equip the diagnostic rooms—step 1—on the one hand, and the radiotherapy treatment rooms—step 2—on the other hand. They can be of two different types.

In the diagnostic rooms, they are used to guide the manipulators which enable the latter to apply the marking to the skin of the patients: this is the first step of the treatment.

In the treatment rooms, they are used to position the patient in the accelerator: this is the last step of the treatment.

The diagnostic rooms also house the virtual simulation. It is in these rooms that the tumor will be perfectly identified and located using an appropriate machine, the scanner.

A standard installation of known type consists of 5 moving lasers placed on either side of the table of the scanner which will generate 5 laser beams, in this case one beam per laser. The five lasers are driven by a computer system present in the control room.

The lasers form three distinct planes, namely a horizontal plane, a substantially transversal vertical plane, these two planes forming a cross, and yet another vertical plane which is generally perpendicular in the axis of the table, the so-called sagittal axis.

The abovementioned vertical beams have to be merged in a single plane. This plane must be perfectly vertical and parallel to the vertical plane of the machine isocenter. The horizontal beams have to be merged in a single plane. This plane must be perfectly horizontal and perpendicular to the vertical plane of the machine isocenter. The sagittal beam has to be perfectly vertical and perpendicular to the vertical plane of the machine isocenter,

PRIOR ART

For this, there are known laser adjustment systems, as described in French document FR-2770763-A1, which, however, do not have any external measurement means, which is reflected in an absence of control which is nevertheless proving important, even essential.

There is also another more recent device consisting of a laser positioning monitoring system on a diagnostic and/or therapy apparatus as described in DE-10200602168-A1 disclosing a device comprising a so-called LAP apparatus which is made up of three distinct elements: a first cube making it possible to visualize the isocenter of the scanner after the acquisition of images, a second cube comprising the sensors for acquiring the positions of the laser beams and a support accommodating the two cubes. The methodology described consists in placing the support on the table of the scanner and then putting the cube in place. An image acquisition session is then initiated, and after a number of manipulations of the support, the final position is validated, the position in which the support is perfectly perpendicular to the isocenter plane of the scanner. The first cube is then removed and the second cube is put in place on the support. The external lasers are then switched on and their position is measured by the linear sensors placed on the second cube.

The document EP 1854412-A1 discloses a device which is made up of 3 distinct blocks in which the first block serves as a support for the other two. On this support is placed the first device 38 which makes it possible to adjust the assembly relative to the isocenter of the machine. Once this adjustment has been made, the second block 22 is put in place. On this second block, there are sensors, 16 of them, which analyze the position of the laser beams. The latter are then adjusted but there is no stipulation as to how. Of course, this document discloses the acquisition of images making it possible to control the position of a device by virtue of the presence of a centering ball, as well as the position of the laser beams being determined by virtue of the cells or sensors embedded in another apparatus, and also the adjustment of each laser beam. Furthermore, this document also discloses two quite distinct devices, namely a device with a centering ball and another device with position sensors, which entails changing the device and a number of manipulations on the part of the operators. This consequently adds work to the manipulation procedure, which poses a problem in this type of intervention.

Thus, at the present time, there are on the market comparable laser positioning systems, for which the proposed technology is close to that proposed hereinbelow. These systems all consist of optical heads, which generate the abovementioned laser beams and which are mounted on more or less efficient rails. The color of the laser beams is set once and for all on installation of the systems for the user. A specific tool is then used for the adjustment of the system, the positioning of the lasers. This tool is generally used only by the employees of the supplier of the system. The final positioning accuracy is of the order of a millimeter. It follows that the adjustment of the current systems is very tricky and often requires specialist personnel, which can be detrimental to the overall flexibility, as well as to its operating cost. Furthermore, the design of the rails used and the system adjustment principle do not make it possible to guarantee either the repeatability or the reliability of the measurements. Moreover, there is no information making it possible to check that the laser beams are truly in the position requested by the operator.

To this is added the fact that the color of the beams sometimes makes identification difficult on certain skin colors. Finally the associated driver software is sometimes extremely restricted and very far removed from the quality assurance standards of a hospital environment.

The American U.S. Pat. No. 4,123,660 dated Oct. 31, 1978 discloses, for its part, an optical apparatus which makes it possible to check the alignment of the lasers in an accelerator room, which, however, has little impact with the automatic system targeted here.

Moreover, document US 2011/001987 dated Jan. 6, 2011 discloses an apparatus generating a cross from a laser source diode that is unrelated to the device targeted according to the present invention.

The same applies to the document GB 24 43 432 A dated Oct. 31, 2006, which discloses a hand-held object guiding apparatus using rays that is unrelated to the targeted device.

For its part, document EP 0 753 285 A1 does relate to positioning lasers, but this document does not mention a laser beam adjustment apparatus.

All these elements introduce a limitation as to quality which is detrimental to the final effectiveness of the treatment of the patient, which therefore constitutes a significant drawback which should be reduced.

OBJECT OF THE INVENTION

The aim of the present invention is to remedy this absence in the known devices.

SUMMARY OF THE INVENTION

To this end, there is proposed, according to the invention, a method for using an adjustment appliance as defined in the main claim 1 consisting in installing the apparatus on the table of the scanner accompanied by a presetting of the position using the three supporting feet and the embedded spirit levels, a movement of the table of the scanner to position the front face of the apparatus in the plane of the isocenter of the scanner, and a positioning using the internal lasers of the scanner, as well as an acquisition of images. The images obtained make it possible to check the correct position of the apparatus by virtue of the various centering balls present on the front face.

Then, the position of the apparatus is finalized. Once the position is validated, the table of the scanner is moved by the nominal distance between the machine isocenter and the laser isocenter. This distance is set. It is determined and validated at the time of installation of the lasers.

The apparatus is connected to a tablet PC controlling the positions of the lasers and it is powered up, with the lasers being powered up and the positions re-set to zero.

The laser beam search sequence is started up by multiplexing. The position of each laser is then determined by virtue of the embedded cells in the apparatus.

The acquisition of the values is done and the transfer to the tablet PC of the adjustment phase of each laser beam.

Indeed, its major specific feature is closely linked to the particular nature of the apparatus for implementing the method, and as a result requires a precise definition of each of the steps of use of the apparatus according to the invention.

The present invention also relates to the apparatus for using, respectively for implementing, the method as defined in the main device claim. Thus, the apparatus according to the present invention consists of a single assembly consisting of seven distinct parts and assembled in a non-dismantleable manner. It includes both the 12 position cells and an electronic control board. Its design is unique, mainly by the fact that it consists of a single block instead of three, or even more than three. This architecture thus avoids several operator manipulations, which at the same time significantly reduces the risk of human error and increases the reliability of the final result.

According to an additional embodiment of the device according to the invention called optical head, it comprises two laser elements generating a beam that is colored red or green, as chosen by the operator. By this measure, a reliable and stable component is obtained.

Bringing together the two features in a single device avoids having to change the device and thus avoids a number of manipulations on the part of the operators by virtue of the method, respectively device, targeted according to the present invention. This solution must thus be considered noteworthy, particularly as it proposes moving the table of the scanner by the nominal distance between the machine isocenter and the laser isocenter.

According to an advantageous embodiment of the device according to the invention, it incorporates two standard industrial laser elements.

According to a particularly advantageous embodiment of the device according to the invention, it is equipped on its base with three adjustable feet allowing for an azimuth adjustment on the table of the scanner.

According to another advantageous embodiment of the device according to the invention, spirit levels are also positioned on the base plate to assist in the positioning by the operators.

According to a still further advantageous embodiment of the device according to the invention, the apparatus is provided with articulation means, such as hinges, making it possible to fold it so as to be able to transport it more easily. In practice, it is a portable apparatus, thus giving it an ease of use. Furthermore, it is all the more portable as it is made up of a single block instead of several.

According to a preferred embodiment of the device according to the invention, it is dedicated to the automatic adjustment of the system with integrated measurement cells and dimension calculated for best accuracy. This particular feature according to the invention offers the advantage of an accurate measurement of the position of each beam and adjustment of each beam relative to one another, as well as an overall and automatic adjustment of the system in closed loop mode using driver software.

Thus, by virtue of the solution provided by the invention, all of the system according to the invention is based on obtaining a guaranteed positioning result, namely a considerably reinforced final accuracy which is even better than 0.1 mm.

The proposed system is made reliable by significantly reducing the number of interventions on the part of the installer for reasons of failure or malfunction.

The system according to the invention provides a significantly greater availability of the rooms equipped with this system.

The latter offers a laser beam color which is left to the choice of the operator and which is instantly interchangeable.

The system allows for an automatic adjustment thereof, through the use of a dedicated tool and with extreme speed, in a few seconds.

Another advantage offered according to the invention is a measurement of position of each laser beam which is extremely accurate, to the hundredth.

Yet another advantage is repeatability and a stability of the system over time which is optimal.

Moreover, the present invention also relates to software for using the apparatus and/or a method for using the invention explained above, which is attached to the present application. In particular, there is proposed dedicated software suited to the constraints of use in a hospital environment.

Thus, the invention provides a suitable response for obtaining an optimum result in terms of treatment and safety for the patient, while observing all the basic recommendations of the Quality system.

According to an additional embodiment of the device according to the invention, there is provided a mechanized optical head with mechanical elements that are simple but perfectly calibrated and designed to give all the necessary degrees of freedom with the maximum accuracy. By virtue of this additional measure, a good reliability and repeatability of the optical system is obtained, together with a stability in time and in temperature, and even a filtering of the external vibratory disturbances.

According to a preferential embodiment of the device according to the invention, there is provided a rail for the movements of the optical head with precision mechanical rolling bearings incorporating a measurement of the position of the optical head on its rail. By virtue of this other measure, an enhanced reliability and an accuracy of the movements of the optical device are obtained, together with a verification of the exact position of the laser beams according to the setpoints given by the operator.

Further properties and particular features of the method and of the device according to the invention are defined in the other respective sub-claims.

Further details and advantages are detailed in the description of a preferred embodiment of the invention given hereinbelow, which is illustrated using the appended drawings, supplied by way of an exemplary non limiting embodiment.

DESCRIPTION

Figure 2:
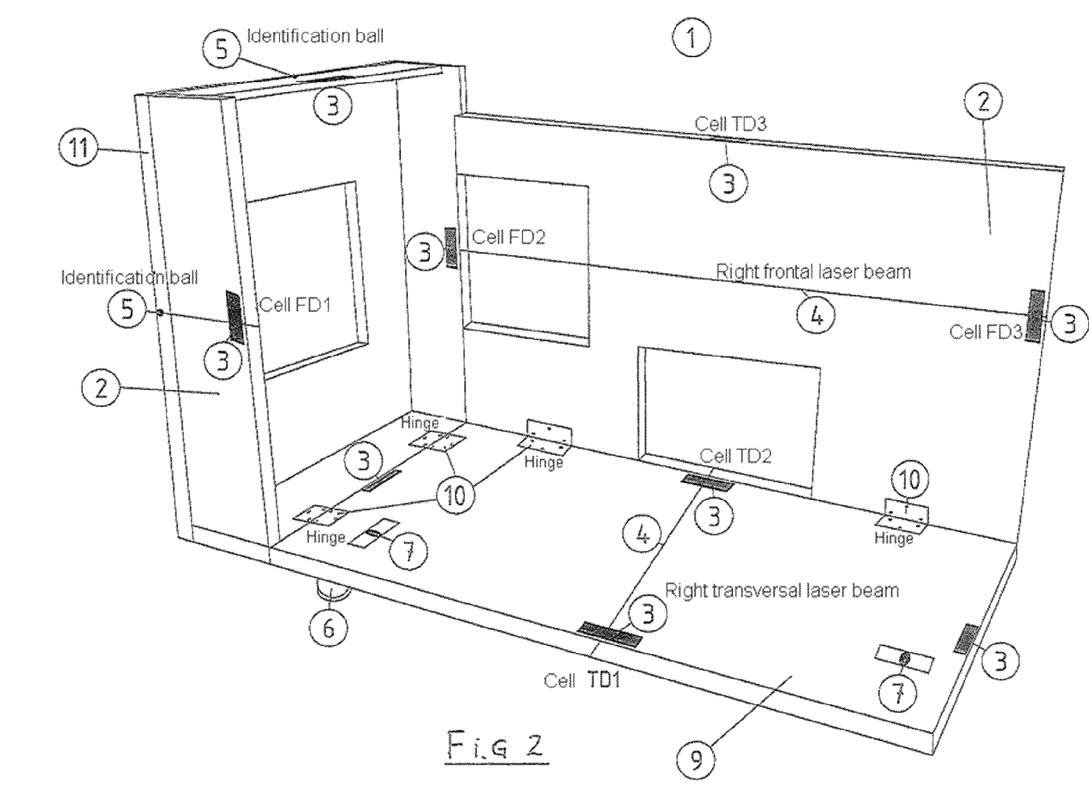
FIG. 2 is a schematic representation of an arrangement of the installation for scanning a patient making it possible to provide a right-hand view of the patient in the system according to the invention.

Generally, the invention relates to a so-called smart apparatus, which consists of a base plate 9 and a number of vertical uprights 2 made of plastic material, as shown in FIG. 2. The apparatus supports a certain number of linear photocells 3 for detecting laser beams 4, preferably around twelve, a certain number of high-density identification balls 5, preferably around five, three supporting feet 6 and two spirit levels 7.

Figure 1:
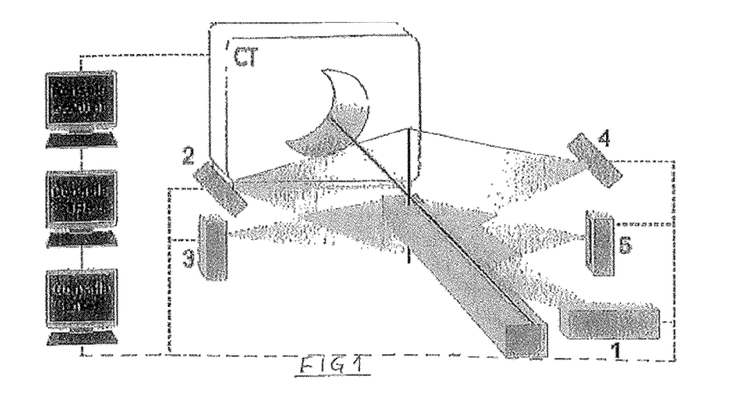
FIG. 1 is a schematic representation of the assembly of an embodiment of the basic device according to the invention.
Figure 3:
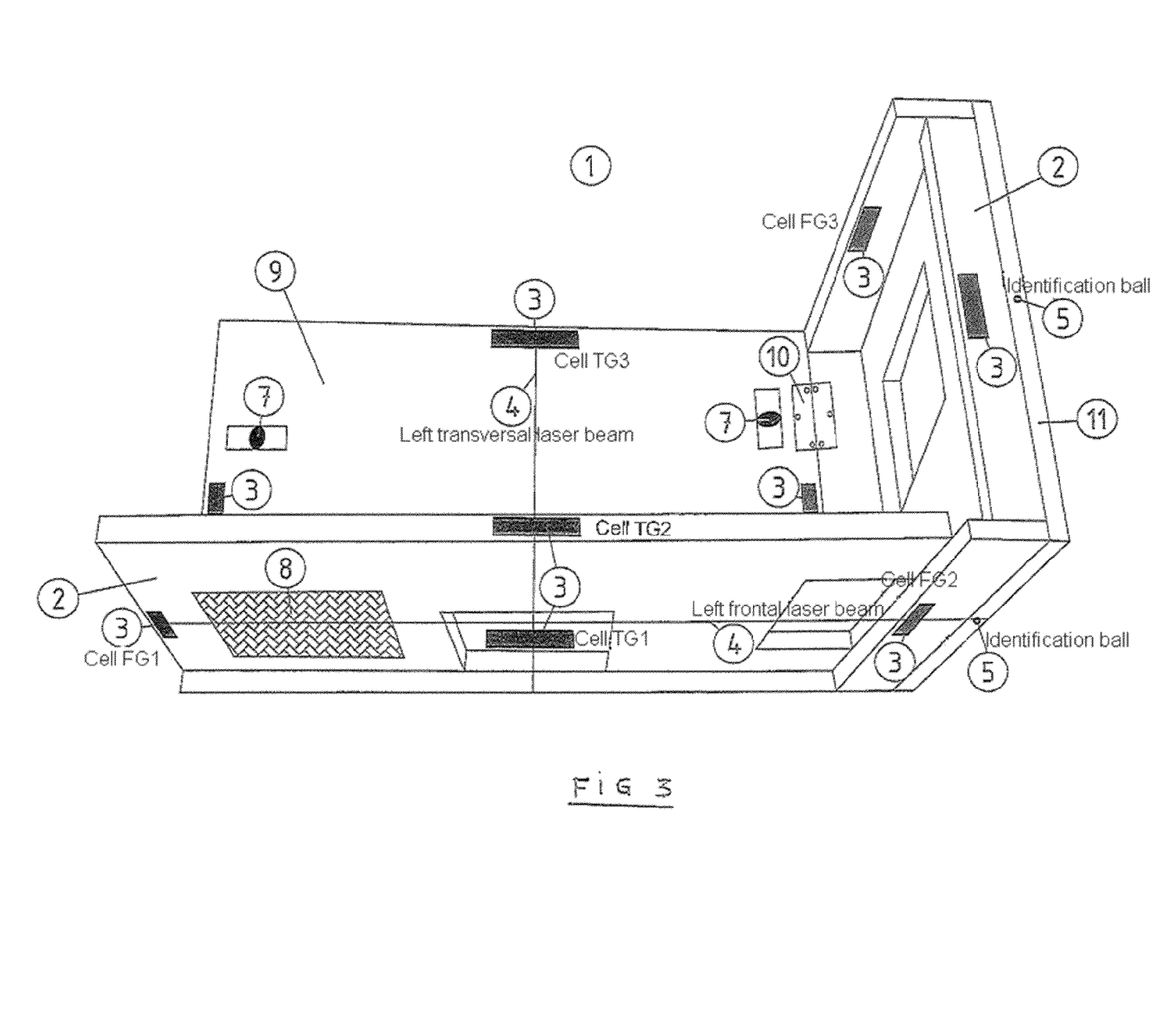
FIG. 3 is a schematic representation of an arrangement of the installation for scanning a patient making it possible to provide a left-hand view of the patient in the system according to the invention.

Each laser beam 4 is projected onto three cells 3 arranged in a volume. The position and exact angle of each beam 4 are thus determined. This information is stored by an electronic control board 8 arranged in the apparatus 1 and shown in FIG. 3. The information is then transmitted to a computer which performs the positioning corrections in real time for each laser beam 4 as shown in FIG. 1.

Figure 4:
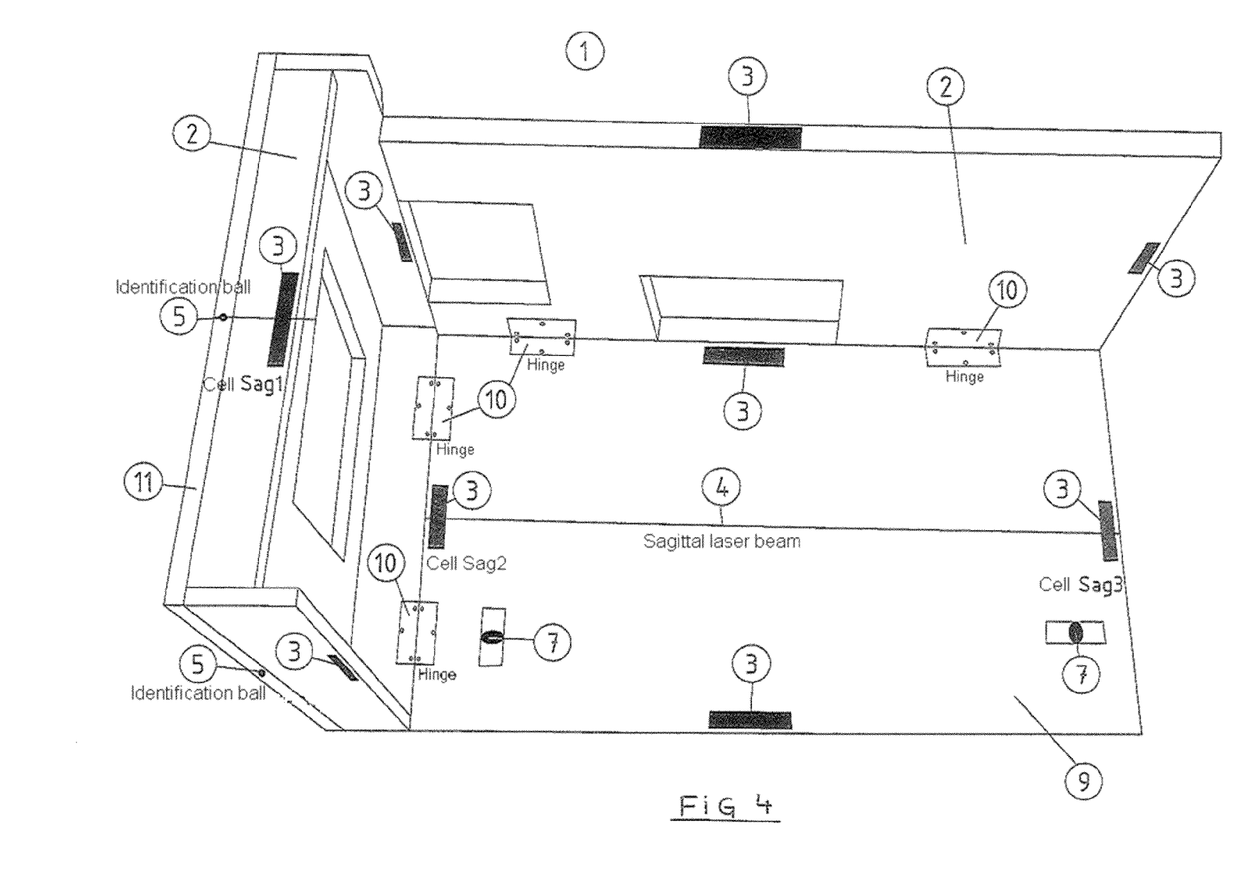
FIG. 4 is a schematic representation of an arrangement of the installation for scanning a patient making it possible to provide a so-called sagittal view of the patient in the system according to the invention.
Figure 7:
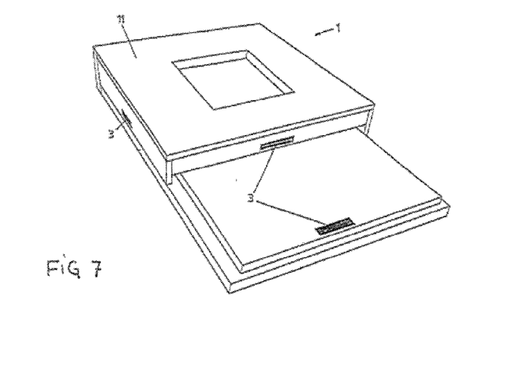
FIG. 7 is a schematic representation of an arrangement of the installation for scanning a patient making it possible to provide a perspective general view, in the folded-down state, in the system according to the invention.

FIG. 4 shows the apparatus 1 provided with hinges 10 making it possible to fold it down so it can be transported more easily. In practice, FIG. 7 shows that it is a portable apparatus, thus conferring upon it an ease of use.

Figure 5:
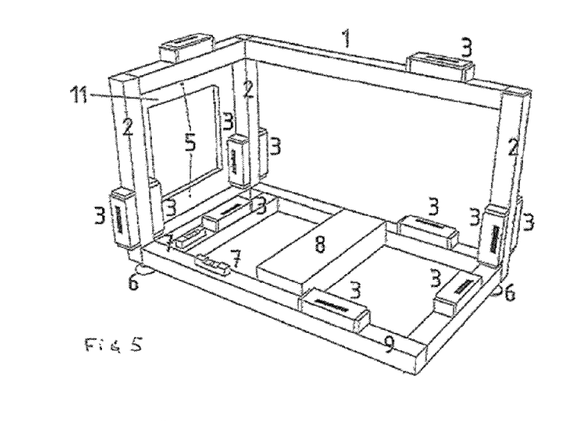
FIG. 5 represents a view similar to the previous latter figures of a preferred variant of the device intended to be used in association with the system according to the invention.
Figure 6:
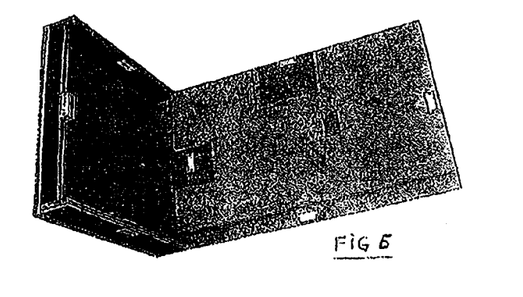
FIG. 6 is a schematic representation of an arrangement of the installation for scanning a patient making it possible to provide a general perspective view, in the unfolded state ready for the use of the patient in the system according to the invention.

FIG. 5 shows the apparatus 1 equipped on its base with said feet which are adjustable 6 allowing for an azimuth adjustment on the table of the scanner. The abovementioned spirit levels 7 are arranged on the base plate 9 to assist in the positioning by the operators.

The procedure for using the basic device is as follows:
placement of the apparatus on the table of the scanner;
presetting of the position using the three support feet 6 and the embedded spirit levels 7;
moving of the table of the scanner to place the front face 11 of the apparatus in the plane of the isocenter of the scanner. Positioning using the internal lasers of the scanner.

acquisition of images. The images obtained make it possible to check the correct position of the apparatus 1 using the five centering balls 5 present on the front face 11.

finalizing of the position of the apparatus 1;

once the position is validated, moving of the table of the scanner by the nominal distance between the machine isocenter and the laser isocenter. This distance is set. It is determined and validated at the time of installation of the laser;

connection of the apparatus 1 with the tablet PC controlling the positions of the lasers;

powering up of the apparatus 1;

powering up of the laser beams 4 with zero resetting of the positions;

starting up of the multiplexing-based laser beam 4 search sequence. The position of each laser beam 4 is then determined using the cells 3 embedded on the device 1;

acquisition of the values and transfer to the tablet PC;

starting up by the tablet PC of the phase of adjustment of each laser beam 4.

FIG. 5 shows the general drawing of the device 1 and in particular the volume that it delimits. The photocells 3 are represented. The adjustment of a beam 4 is obtained from three photocells 3. The photocells 3 are placed shrewdly and ultra-precisely on the device 1 so that, once adjusted, the beams 4 all converge at the same point in space called device isocenter. The identification balls 5 are used to obtain an ultra-precise correlation between the isocenter of the device and the isocenter of the scanner during the system calibration procedure.

Figure 8:
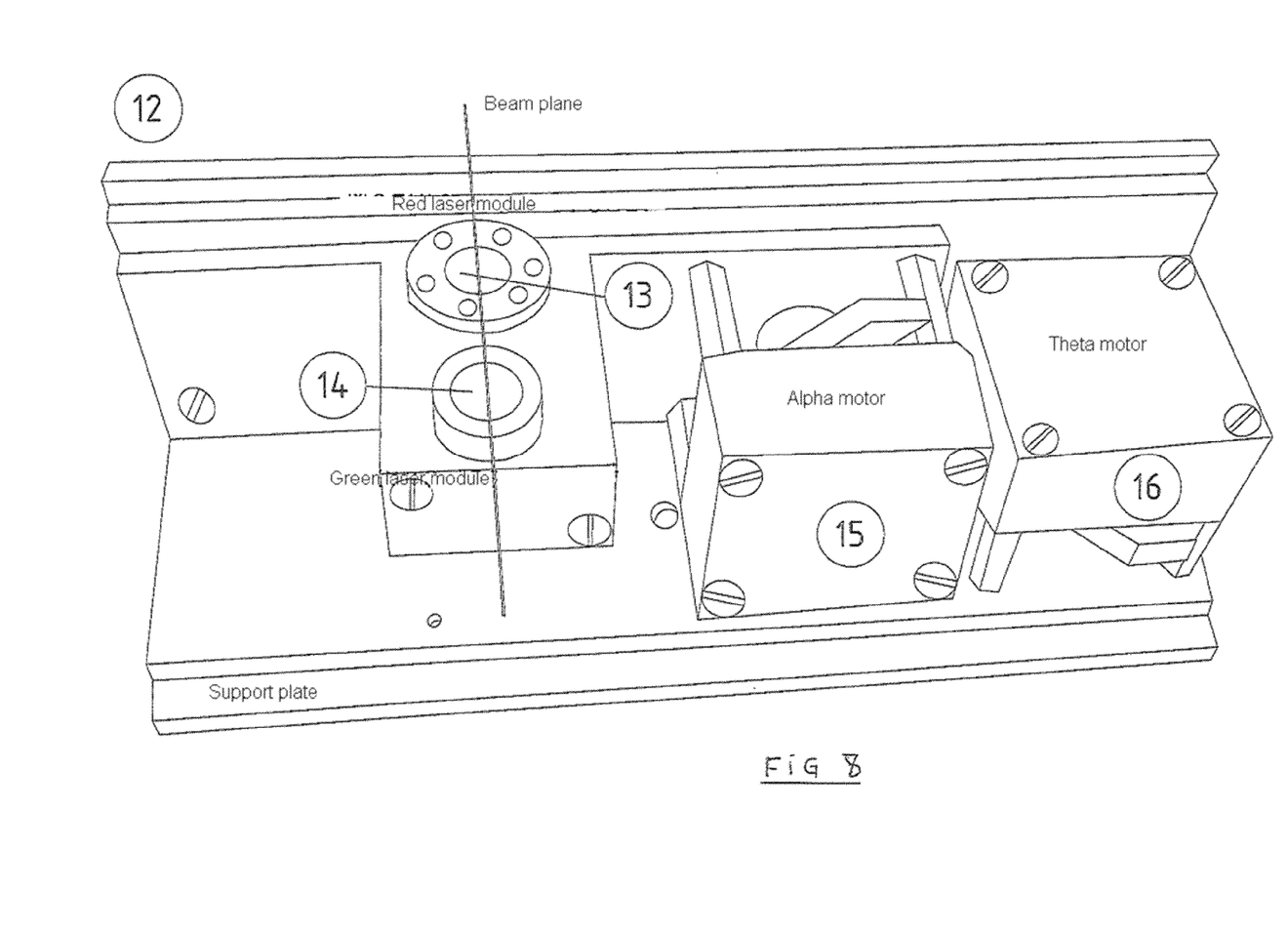
FIG. 8 represents a plan view of a device with optical head provided for use in association with the abovementioned basic system according to the invention.

Additional views are given in FIG. 8 et seq. Once the positions of the laser beams 4 have been acquired by multiplexing, the control board 8 sends its information to the tablet PC. The latter then gives its adjustment commands to the different optical heads 12 that make up the system.

The perfect positioning of the beams 4 is monitored by the abovementioned so-called smart phantom apparatus 1. The patient is placed on the table of the scanner. The moving lasers are powered up and placed at their zero point. A first marking on the skin is made by the manipulators. Once marked, the patient is placed at the center of the tunnel of the scanner and image acquisitions are performed. The tumor is then located by the radiologist and appears on the virtual simulation console (TPS). The doctor will then outline the tumor, therefore determining the exact position values of the tumor in three dimensions. This information is then transmitted electronically to the console driving the moving lasers.

In the meantime, the patient is returned to his or her starting point and therefore once again positioned on the initial point constituting the "0" of the laser beams 4.

The moving lasers are moved on the basis of this information and are placed at the exact isocenter of the tumor. They therefore indicate a new cross. It is this final cross which will be tattooed on the patient by the manipulator and which will serve as a position reference in the treatment room.

Figure 9:
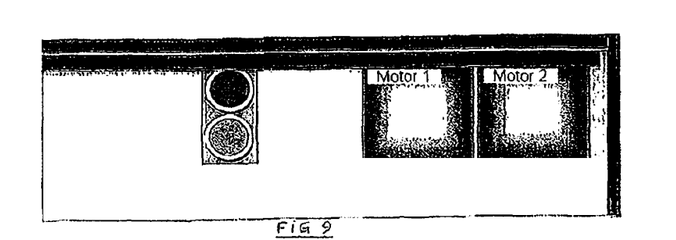
FIG. 9 is a schematic representation of a particular arrangement of the invention.

The invention also relates to an optical device comprising a rail and a head, and to a tool dedicated to the automatic adjustment of the system constituting the smart device, the optical heads 12 also being the subject of the invention. The optical device is made up of the following elements as also illustrated in FIG. 9. A motor-driven rail with precise position measurement to the hundredth of a millimeter and an optical head 12 made up of ultra-precise motors 15 and 16 for the movements according to all the degrees of freedom, passive mechanical elements to support the red 13 and green 14 laser generators and passive support and articulation mechanical elements for the assembly.

Thus, this apparatus with optical head 12 is made up of a mechanical assembly with lever arm, two precision stepper motors equipped with end-of-travel sensors, two laser modules 13 and 14 and an electronic control board.

Figure 10:
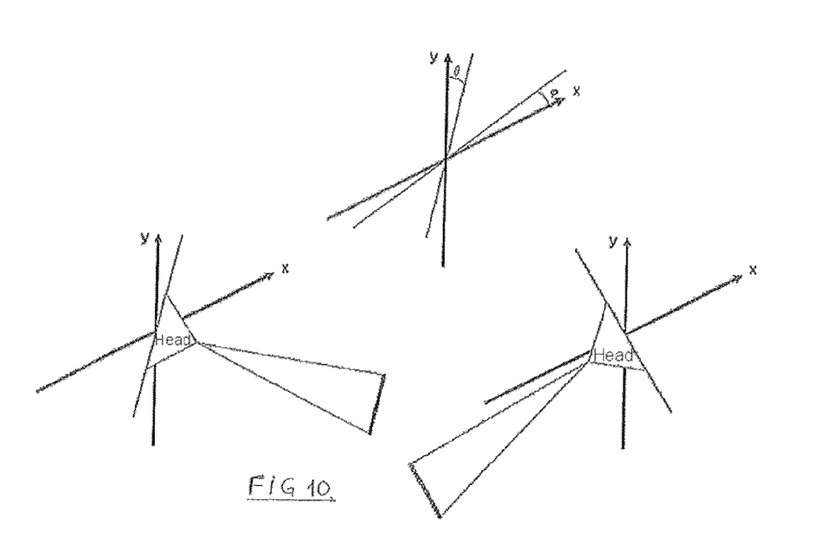
FIG. 10 is a simplified representation of a particular element of the invention.

Two laser modules generate a red colored line 13 and a green colored line 14. These two lines 13 and 14 are merged in one and the same plane. The functionality of the optical head 12 is to be able to orient this plane on two different axes $\alpha$ and $\theta$ represented in FIG. 10. The value of the angles is +/−2° with an accuracy of 10'.

An electronic board which is driven by a ZigBee radio link, receives the information from the central CPU and controls the two stepper motors 15 and 16.

Furthermore, there is also provided driving software which very accurately and securely drives all the systems installed on the client sites, for which the general description is outlined hereinbelow by way of example.

EXAMPLE

This software is run in a Microsoft Windows network environment on computers of desktop PC and tablet PC type. The software is developed under Microsoft Visual Basic (Studio 2010) and operates an SQL-type database. All the functionalities of said software can be accessed via a pop-up menu.

Figure 11:
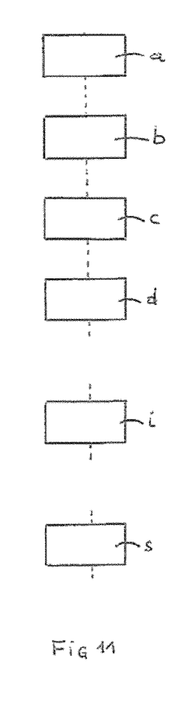
FIG. 11 is a simplified block diagram representation, representing modules that make up the functionalities of the software used in the arrangement of the invention.

FIG. 11 shows a partial block diagram of a detail of the software functionalities, used wholly or partly, possibly in a different order, listed hereinbelow:

a) Parameterization of the software: this module makes it possible to manage all the software data operating parameters.

b) User management: this module makes it possible to manage the creation, the updating, the deletion and printing of data specific to the program users. Each user is provided with a program access level.

c) System logging: use of each of the functionalities and all the alarms detected are the subject of a record in a log.

d) Online help: this software is provided with a context-sensitive "User Guide" (key F1) which can be viewed at any time on the screen of the tablet PC or on the desktop PC. This "user guide" details all the functionalities of the software. All or part of this "user guide" can be printed at the request of the user.

e) Alarm management: in the event of a malfunction of one or other of the components of the system and detected by the software, the latter switches to "System fault mode". A pop-up list of the faults listed is displayed on the screen. Alongside each fault, setpoints guide the user in what to do.

f) Backup/restore operating data: this module makes it possible to backup automatically, or at the request of the user, all of the program database. This backup can be performed, at the choice of the user, on an external medium (USB key, CD-ROM) or on a network disk. The restoration of all of the database is performed at the request of the user. The latter has the option to choose the backup file to be used for the restore function.

g) Patient and session management: the software makes is possible to create, manually by input, a number of patients, a number of fields (tumors) for each of these patients, a number of positioning points for each of these fields, and to automatically create the patients, fields and positioning points from data imported from the text-format TPS files.

The object of a treatment session is to position the laser beams in accordance with the TPS setpoints (positioning points) in order to proceed with the marking on the skin of the patient. The software therefore makes it possible, in the context of a patient's treatment sessions, to     select a patient in the database,
        for this patient, select a field (tumor) in the database, and
        for this field, select one or more positioning points in the database.

If a number of positioning points are selected by the operator, the latter is prompted to choose a manual sequencing or a time-delayed sequencing of the driving of the laser beams. In the manual case, the transition from one positioning point to the next is activated by the operator as embodied in a click on a "next point" button on the screen. In the time-delayed case, the time-delay value for the transition from one positioning point to the next is entered by the operator at the start of the session.

For each positioning point previously selected by the operator:
the program displays on the screen the information specific to the positioning point (coordinates, description, etc.),
the operator is prompted to authorize (click a button on the screen) the driving of the laser beams by the program,
the program drives the laser beams on the basis of the positioning set point values,
the marking on the skin is done manually by the operator,
the operator is prompted to validate the operation (click a button on the screen),
the operation is stored in a history file of the patient treatment sessions.

h) TPS data recovery: each time the patient passes through the scanner, the operator proceeds with outlining the tumor by dots. Thus, a file is generated by the TPS console computer system. This DICOM RT standardized file contains numerous data, notably scanner data header; patient data; fields (tumors) and coordinates of the target points of each field for treatment in radiotherapy.

The software recovers the above data and incorporates them in its own database.

i) Display/print operating data: all the information concerning the operating data can be displayed on the screen of the tablet PC or of the desktop PC.

j) Equipment management: the software makes it possible to control the creation, the updating and the printing of all the configuration data of the equipment that make up the system of the invention on each operating site.

k) Equipment self-test: on starting up the software and after authentication of the user, a self-test is carried out by the program to check the integrity of the system. This self-test can also be launched at the request of the user.

l) Selection of the laser beam colors: the software makes it possible to select, at any time and in any of the modules of the program, the color (green, red or none) of each of the laser beams, individually or for all of the beams.

m) Manual equipment calibration: the manual calibration of each of the laser beams (motor-driven HITs and moving HITs) makes it possible to adjust and calibrate the system during its installation, and do so in light of the physical characteristics of the installation site. This operation can also be carried out in maintenance mode by a competent technician or by an operator when a check on the adjustments and the calibration is required.

The software keeps a historical log recording all the modifications made on calibrating any of the laser beams.

n) Automatic equipment calibration: the automatic calibration of each of the laser beams (motor-driven HITs and moving HITs) is carried out with the use of the abovementioned so-called smart phantom equipment. This equipment is a smart system provided with sensors (photoreceivers) which record the position of each of the beams in service. The phantom is therefore interrogated by the software which, given the information collected, automatically drives the laser beams according to the desired orientations (coincidence of the laser beams) and to the positions sought (isocenter). The software keeps a historical log recording all the modifications made on calibrating any of the laser beams.

o) Calibration of the axes: the software includes the calibration functionality for each of the laser beams (motor-driven HITs and moving HITs) operated in the system. This calibration makes it possible to obtain an accuracy of 0.1 mm of linear movement of each of the laser beams on the skin of the patient. A calibrator (moving sensor) is used to calibrate the axes.

p) Laser beams initialization: the software carries out a laser initialization sequence in the following cases: when the program is started up once the self-test has been successfully carried out and/or at the request of the user.

This initialization sequence performs the following operations:
    positioning of each of the laser heads at the origin of the axes.
    Positioning of each laser head in light of the calibration data. The user will be informed of the correct execution of the laser beams initialization sequence.

q) TPS setpoints: the software is able to position the laser beams in light of setpoints linked to positioning points selected by the user.

These positioning points correspond to the target points derived from the TPS data.

The laser beams being positioned at the laser isocenter, or already having been the object of a TPS setpoint, these beams are moved in light of the coordinates indicated by these positioning points.

r) Patient placement: this module makes it possible to individually move the so-called "sagittal" laser beam to the left or to the right of the patient for a specific marking on the skin. This marking on the skin does not correspond to a positioning point derived from TPS data.

The value of the movement of the laser beam is entered (unit=cm) by the operator. A number of movements can thus be performed to position the "sagittal" beam prior to the marking on the skin.

s) Display/print equipment data: all the information concerning the equipment data can be displayed on the screen of the tablet PC or of the desktop PC. The output of this information to a printer can be requested by the user.

The invention claimed is:

1. A method for adjusting laser beams (4) for scanners arranged on a support, notably dedicated to radiotherapy, which is positioned on said support, by means of a device which consists of a single one-piece assembly (1) comprising a certain number of distinct parts, and assembled in a non-dismantleable manner, which includes both a certain number of position sensors (3), and an electronic control board (8) suited to the one-piece structure of said assembly (1), said sensors (3) making it possible to visualize the exact position of said beams (4), so as to accurately adjust them automatically by motor-driven systems, wherein it comprises the following steps:
    installing the apparatus (1) on the table of the scanner;
    presetting the position using the three supporting feet (6) and the embedded spirit levels (7);
    moving the table of the scanner to position the front face (11) of the apparatus in the plane of the isocenter of the scanner, and a positioning using the internal lasers of the scanner;

acquisition of images, wherein the images obtained make it possible to check the correct position of the apparatus (1) by using at least 4 centering balls (5) present on the front face (11);

finalizing the position of the apparatus;

once the position is validated, moving the table of the scanner by the nominal distance between the machine isocenter and the laser isocenter, wherein this distance is set, which is determined and validated at the time of installation of the lasers;

connecting the apparatus (1) to a PC tablet controlling the positions of the laser beam (4);

powering the apparatus (1) up, powering the lasers beams (4) up and re-setting the positions to zero;

starting up the laser beam (4) search sequence by multiplexing, wherein the position of each laser beam (4) is then determined using the embedded cells (3) in the apparatus (1);

doing the acquisition of the values and transfer to the tablet PC of the adjustment phase of each laser beam (4).

2. A method according to any preceding claim, wherein said process of use comprises each of said steps being carried out in the specified order.

3. A device for adjusting laser beams (4) for scanners arranged on a support, notably dedicated to radiotherapy, which is positioned on said support, in particular for implementing the method as defined in claim 1, wherein it consists of a single one-piece assembly (1) comprising a certain number of distinct parts, and assembled in a non-dismantleable manner, in that it includes both a certain number of position sensors (3), and an electronic control board (8) suited to the one-piece structure of said assembly (1), said sensors (3) being arranged to visualize the exact position of said beams (4), so as to accurately adjust them automatically by motor-driven systems; the device being equipped on its base (9) with three adjustable feet (6) allowing for an azimuth adjustment of said assembly (1) on the table of the scanner, the latter comprising spirit levels (7) which are positioned on the base plate (9) to assist in the positioning by operators and a certain number of centering balls (5) present on the front face (11).

4. A device according to any preceding claim, wherein it comprises two laser elements (13, 14) generating a beam with a different color which is selectable, particularly red or green, up to the choice of the operator.

5. A device according to any preceding claim, wherein said color of the laser beam is instantly interchangeable.

6. A device according to claim 3, wherein said single block set (1) comprises seven distinct parts, and wherein at least ten, more particularly twelve position sensors (3) are provided.

7. A device according to claim 3, wherein it is a portable apparatus (1).

8. A device according to claim 3, wherein it incorporates two standard industrial laser elements.

9. A device according to claim 3, wherein it includes dedicated software suited to the constraints of use in a hospital environment.

10. A device according to any preceding claim, wherein it comprises integrated measurement cells (3), with dimension calculated for better accuracy, being dedicated to an automatic adjustment of the system for allowing an accurate measurement of the position of each said beam (4), and adjustment of each beam relative to one another, as well as an adjustment in closed loop mode using said software.

11. A device according to claim 5, wherein it has a guaranteed positioning result, with a final accuracy of at least 0.1 mm.

12. A device for adjusting laser beams for scanners on a support dedicated to radiotherapy, in particular according to claim 3, wherein it has at least one mechanized optical head (12) with calibrated mechanical precision elements for ensuring the necessary degrees of freedom.

13. A device according to any preceding claim, wherein it comprises filtering means of the external vibratory disturbances.

14. A device according to claim 12, wherein it comprises guiding means, particularly a rail for the movements of said optical heads (12) with precision mechanical rolling bearings incorporating a measurement of the position of the optical head (12) on its rail.

15. A device according to claim 12, wherein it comprises a mechanical assembly with lever arm, made up of two precision stepper motors (15, 16) equipped with end-of-travel sensors, two laser modules (13, 14) and an electronic control board, which allows for being driven by a radio link, for receiving the information from the central CPU and for controlling the two said stepper motors (15, 16).

16. A device according to claim 3, wherein it comprises controlling means for the verification of the exact position of the laser beams (4) according to the setpoints to be given or to provide by the operator.

17. Use of software for carrying out at least part of the steps, respectively, stage of the method according to claim 1, notably by means of a device for adjusting laser beams (4) for scanners arranged on a support, notably dedicated to radiotherapy, which is positioned on said support, in particular for implementing the method as defined in claim 1, wherein it consists of a single one-piece assembly (1) comprising a certain number of distinct parts, and assembled in a non-dismantleable manner, in that it includes both a certain number of position sensors (3), and an electronic control board (8) suited to the one-piece structure of said assembly (1), said sensors (3) being arranged to visualize the exact position of said beams (4), so as to accurately adjust them automatically by motor-driven systems; the device being equipped on its base (9) with three adjustable feet (6) allowing for an azimuth adjustment of said assembly (1) on the table of the scanner, the latter comprising spirit levels (7) which are positioned on the base plate (9) to assist in the positioning by operators and a certain number of centering balls (5) present on the front face (11), wherein it has modules forming the functionalities of the software used wholly or partly, possibly in a different order, which are listed herein below:

a) Parameterization of the software allowing managing all the software data operating parameters;

b) User management allowing managing the creation, the updating, the deletion and printing of data specific to the program users, wherein each user is provided with a program access level;

c) System logging, wherein the use of each of the functionalities and all the alarms detected are the subject of a record in a log;

d) Online help, wherein the software is provided with a context-sensitive "User Guide", which can be viewed at any time on the screen of the tablet PC or on the desktop PC and which details all the functionalities of the software;

e) Alarm management, wherein in the event of a malfunction of one or other of the components of the system and detected by the software, the latter switches to "System fault mode", wherein a pop-up list of the faults listed is displayed on the screen and, wherein alongside each fault, setpoints guide the user in what to do;

f) Backup/restore operating data, allowing to backup automatically, or at the request, all of the program database;
g) Patient and session management allowing creating manually by input a number of patients, a number of fields notably tumors for each of these patients, a number of positioning points for each of these fields, and automatically creating the patients, fields and positioning points from data imported from the text-format TPS files;
h) TPS data recovery, wherein each time the patient passes through the scanner, the operator proceeds with outlining the tumor by dots, wherein a file is thus generated by the TPS console computer system, wherein the software recovers the above data and incorporates them in its own database;
i) Display/print operating data, wherein all the information concerning the operating data can be displayed on the screen;
j) Equipment management, wherein the software allows controlling the creation, the updating and the printing of all the configuration data of the equipment that make up the system of the invention on each operating site;
k) Equipment self-test, wherein on starting up the software and after authentication of the user, a self-test is carried out by the program to check the integrity of the system, wherein said self-test can also be launched at the request of the user;
l) Selection of the laser beam colors, wherein the software allows selecting, at any time and in any of the modules of the program, the color (green, red or none) of each of the laser beams, individually or for all of the beams;
m) Manual equipment calibration, wherein the manual calibration of each of the laser beams (motor-driven HITs and moving HITs) allows adjusting and calibrating the system during its installation, and do so in light of the physical characteristics of the installation site;
n) Automatic equipment calibration, wherein the automatic calibration of each of the laser beams—motor-driven HITs and moving HITs—is carried out with the use of the above-mentioned so-called smart phantom equipment, wherein it is a smart system provided with sensors or photoreceivers which record the position of each of the beams in service, wherein said system is interrogated by the software which, given the information collected, automatically drives the laser beams according to the desired orientations by coincidence of the laser beams, and to the positions sought in Isocenter, wherein the software keeps a historical log recording all the modifications made on calibrating any of the laser beams;
o) calibration of the axes, wherein the software includes the calibration functionality for each of the laser beams—motor-driven HITs and moving HITs—operated in the system, wherein this calibration allows obtaining an accuracy of up to 0.1 mm of linear movement of each of the laser beams on the skin of the patient, wherein a calibrator or moving sensor is used to calibrate the axes;
p) Laser beams initialization, wherein the software carries out a laser initialization sequence in the following cases: when the program is started up once the self-test has been successfully carried out and/or at the request of the user, wherein said initialization sequence performs the operations of positioning each of the laser heads at the origin of the axes, respectively, positioning of each laser head in light of the calibration data, wherein the user is informed of the correct execution of the laser beams initialization sequence;
q) TPS setpoints, wherein the software is able to position the laser beams in light of setpoints linked to positioning points selected by the user, wherein these positioning points correspond to the target points derived from the TPS data, wherein the laser beams are positioned at the laser isocenter, or already having been the object of a TPS setpoint, these beams are moved in light of the coordinates indicated by these positioning points;
r) patient placement allowing individually moving the so-called "sagittal" laser beam to the left or to the right of the patient for a specific marking on the skin, wherein the value of the movement of the laser beam is entered by the operator; and
s) display/print equipment data.

18. Use according to any preceding claim, wherein the process of use comprises each of the steps carried out according to said software, particularly in the specified order.

19. Use according to claim 17, wherein the output of all or part of this information on a printer can be requested by the user.

* * * * *